US 6,320,928 B1

(12) United States Patent
Vaillant et al.

(10) Patent No.: US 6,320,928 B1
(45) Date of Patent: Nov. 20, 2001

(54) METHOD OF RECONSTRUCTION OF A THREE-DIMENSIONAL IMAGE OF AN OBJECT

(75) Inventors: Régis Vaillant, Villebon sur Yvette; Yves Trousset, Palaiseau; Romain Boucherie, Meudon; René Romeas, Palaiseau, all of (FR)

(73) Assignee: GE Medical Systems, S.A. (FR)

( * ) Notice: Subject to any disclaimer, the term of this patent is extended or adjusted under 35 U.S.C. 154(b) by 0 days.

(21) Appl. No.: 09/254,094

(22) Filed: Mar. 1, 1999

Related U.S. Application Data

(63) Continuation of application No. PCT/FR97/01554, filed on Sep. 3, 1997.

(30) Foreign Application Priority Data

Sep. 4, 1996 (FR) .................................................. 9610774

(51) Int. Cl.⁷ ...................................................... A61B 6/00
(52) U.S. Cl. ................................. 378/4; 700/98; 700/182
(58) Field of Search ............................. 700/98, 118, 182, 700/120; 345/419, 420; 382/133, 130; 378/4, 901

(56) References Cited

U.S. PATENT DOCUMENTS

| 4,969,469 | * | 11/1990 | Mills .................................... 600/409 |
| 5,241,471 | * | 8/1993 | Trousset et al. ...................... 382/274 |
| 5,588,032 | * | 12/1996 | Johnson et al. .......................... 378/8 |
| 6,005,916 | * | 12/1999 | Johnson et al. ........................ 378/87 |

FOREIGN PATENT DOCUMENTS

| 8903606 | 9/1990 | (FR) . |
| 8916906 | 6/1991 | (FR) . |
| 9300804 | 7/1994 | (FR) . |

OTHER PUBLICATIONS

Parker et al, "Three-Dimensional Reconstruction and Flow Measurements of Coronary Arteries Using Multi-view Digital Angiography" New Developments in Quantitative Coronary Angiography, J.C. Riebor, P.W. Surreys, Eds. pp 225–247, Kluwor Academic Publishers, 1988.

D.J. Hawkes et al. "The Accurate 3–D Reconstruction of the Geometric Configuration of the Vascular Trees From X–Ray Recordings", Physics And Engineering of Med/Caz Imaging, R. Guzzardi, Ed, Nijhaffi 1987.

Garremi et al. "A Knowledge-Based Approach for 3-D Reconstruction and Labeling of Vascular Networks From Biplane Angiographic Projections", IEEE Medical Imaging, vol. 10, No. 2, pp 122–131, Jun. 1991.

Gordon et al, "Algebraic Reconstruction Techniques (ART) for Three-Dimensional Electron Microscopy and X–ray Photography", Journal of Theo. Biol (1970) vol. 29, pp 971–981.

Fundamentals of Digital Image Processing, Jain, Sep. 1988, Engineering/Science/Mathematics.

(List continued on next page.)

*Primary Examiner*—William Grant
*Assistant Examiner*—Zoila Cabrera
(74) *Attorney, Agent, or Firm*—Jay L. Chaskin

(57) ABSTRACT

A set of digital two-dimensional projected images of an object is acquired for different positions of a camera rotating around an object. The projected images are calibrated into a volume containing the object and divided into voxels, the space coordinates of which are identified in a chosen calibration frame of reference. A pretreatment is applied on each acquired image in order to elaborate a rectified image having a predetermined spatial orientation selected as a function of a chosen specific axis of the calibration frame of reference, and an iterative algorithm of algebraic image reconstruction between each rectified image and the set of voxels is applied by successively treating the voxels in a predetermined order linked to the choice of said specific axis, which makes it possible to minimize the duration of reconstruction of the three-dimensional image.

12 Claims, 2 Drawing Sheets

OTHER PUBLICATIONS

Figure 1:
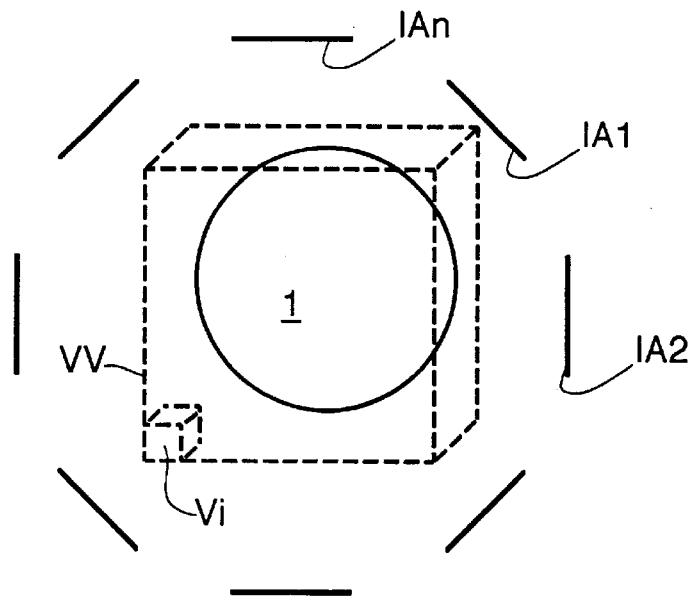

Garcia, I et al, "Implementation and Experimental Evaluation of the Constrained Art Algorithm on a Multicomputer System," Signal Processing, vol. 51, No. 1, May 1, 1996, pp 69–76.

Herman, G.T. et al, "Algebraic Reconstruction Techniques Can be Made Computationally Efficient", IEEE Trans. on Medical Imaging, vol. 12, No. 3 Sep. 1, 1993, pp 600–609.

Payot et al, "An Adaptative and Constrained Model For 3D X–Ray Vascular Reconstruction", Proceedings of the 1975 International Meeting on Fully Three Dimensional Image Reconstruction in Radiology and Nuclear Medicine, Jul. 4, 1995, France.

* cited by examiner

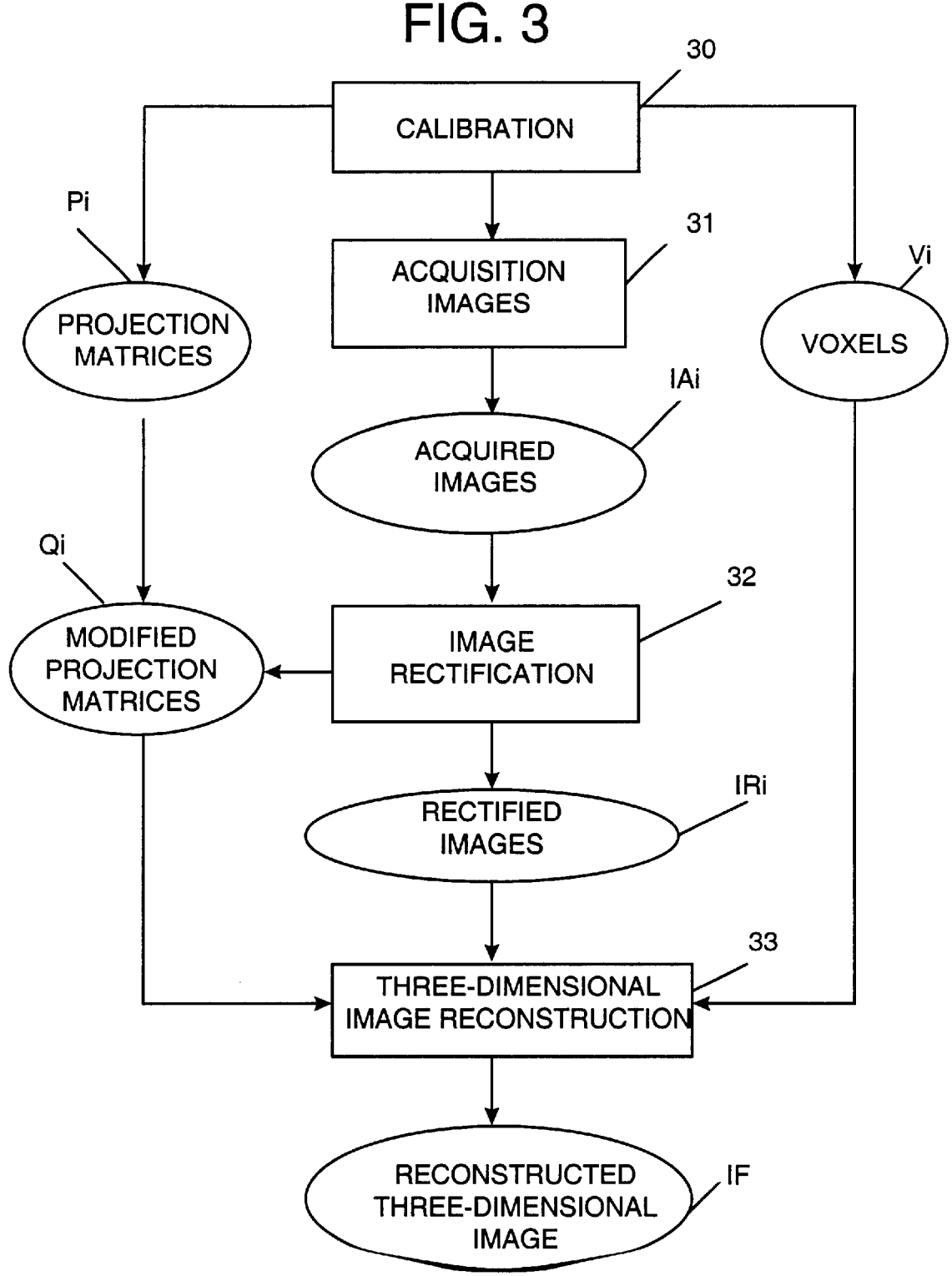

METHOD OF RECONSTRUCTION OF A THREE-DIMENSIONAL IMAGE OF AN OBJECT

This is a continuation application of International Application No. PCT/FR97/01554 filed Sep. 3, 1997.

BACKGROUND OF THE INVENTION

The invention concerns the reconstruction of a three-dimensional image of an object from a set of two-dimensional projected images of the object obtained for different positions of a camera around the object.

Its application is of particular interest in the medical field, in which reconstruction of the internal structures of a patient being examined is undertaken, and especially the reconstruction of angiographic images, that is, to obtain images of vascular trees opacified by injection of a contrast product.

The invention can, however, find applications in other fields, notably, in nondestructive industrial control, in which examinations of the same type as medical examinations are performed.

In the medical field two-dimensional projected images of the object, a patient's head, for example, are generally obtained by rotation of an X-ray camera turning around the object There are essentially two types of reconstruction algorithms in X-ray imaging.

A first type provides for a calculation of back projection and filtering or even a reconstruction by Fourier transform in several dimensions.

A second type, involved in the present invention, concerns iterative methods of reconstruction also called algebraic. The principle of such an algebraic algorithm is well known to the expert and has already been the subject of numerous published papers. One can notably cite Gordon, Bender and Herman, "Algebraic Reconstruction Technic for Three-Dimensional Electron Microscopy and X-ray Photography," Journal THEO. BIOL. 29, pages 471 to 781 (1970); Anil K. Jain, "Fundamentals of Digital Image Processing," Prentice Hall Information and System Sciences Series, Thomas Kailath Series Edition, or French patent Applications Nos. 89 03606 or 89 16906.

After a calibration of the camera used to determine, notably, the parameters of projection in the projection planes of the acquired images, of an observed volume broken down into elementary volume elements or voxels (those calibration parameters forming projection matrices), the algebraic image reconstruction algorithm is used to reconstruct the three-dimensional volume from those two-dimensional projected images. The basic principle of the algorithm is to initialize the voxels of the volume to a predetermined initial value, a zero value, for example, and to repeat a number of times the following operations: projection of voxels in the plane of each acquired image so as to obtain a virtual image, determination of the difference between the projected volume (virtual image) and the corresponding acquired image and then back projection of the difference in volume. After a number of iterations, an estimated value representative of the density of the contrast product injected in the vessels X-rayed is obtained for each voxel, which makes it possible to visualize in three dimensions the cartography of those X-rayed vessels.

Such an algorithm necessitates determining a great number of times, typically several million times, the projection of a voxel, using the different projection matrices.

If the algorithm is not optimized, determination of the projection of a voxel requires at least nine additions, ten multiplications and one division, which is a severe drain on the calculation time of the microprocessor incorporating the algorithm and, consequently, on the duration of image reconstruction.

BRIEF SUMMARY OF THE INVENTION

An embodiment of the invention optimizes the time of calculation of the image reconstruction algorithm and consequently reduces the time necessary for reconstruction of the three-dimensional image.

An embodiment of the invention is thus intended to reduce to a single addition the number of operations necessary for the determination of projection of a current voxel, knowing the projection of the previous voxel.

An embodiment of the invention therefore proposes a method of reconstruction of a three-dimensional image of an object from a set of digital two-dimensional projected images of the object obtained for different positions of a camera around the object. The embodiment of the method may include a calibration of the camera, an acquisition of the set of digital two-dimensional projected images and a reconstruction of the three-dimensional image from the projected two-dimensional acquired images and an iterative algorithm of algebraic image reconstruction. According to a general characteristic of an embodiment of the invention, the calibration stage a volume containing the object is broken down into voxels, the space coordinates of which are identified in a so-called chosen "calibration" frame of reference. A pretreatment or rectification is applied on each acquired image in order to establish a rectified image having a predetermined spatial orientation selected as a function of a chosen specific axis of the calibration frame of reference, e.g., the mean estimated axis of rotation of the camera around the object. The iterative algorithm of algebraic image reconstruction between each rectified image and the set of voxels is then applied by successively treating the voxels in a predetermined order linked to the choice of said specific axis. The duration of reconstruction of the three-dimensional image is thus minimized.

BRIEF DESCRIPTION OF THE DRAWING(S)

Figure 2:
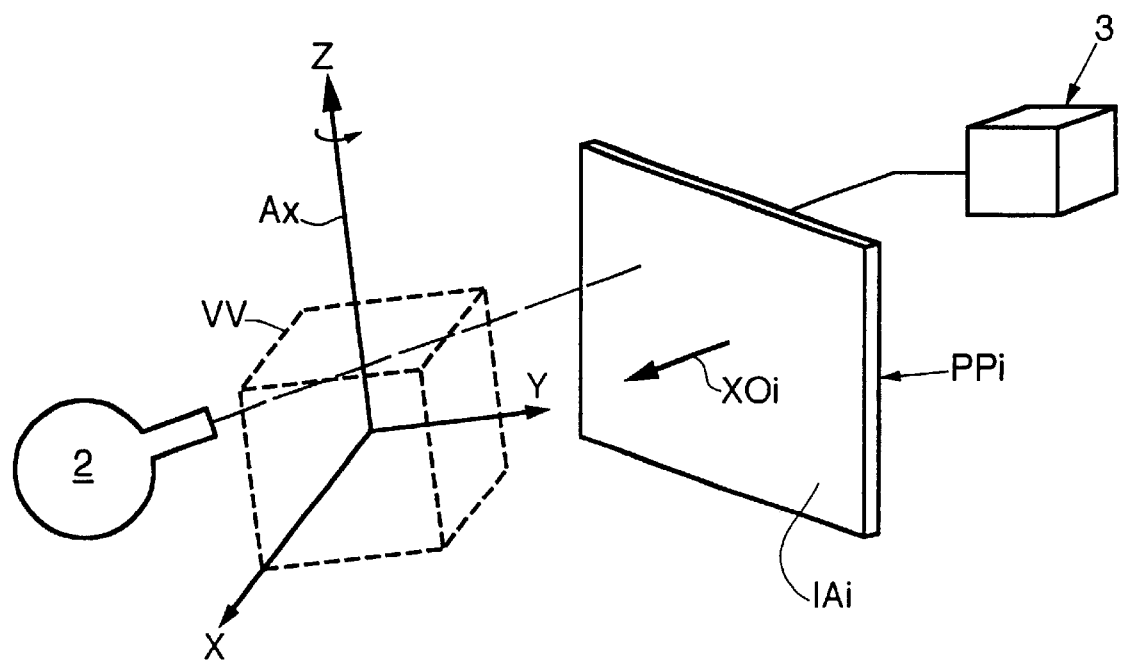

Other advantages and characteristics of the invention will appear on examination of the detailed specification of a not-at-all limitative mode of use and of the attached drawings, on which:

FIG. 1 schematically illustrates a set of two-dimensional projected images around an object;

FIG. 2 illustrates in more detail the acquisition of one of those two-dimensional projected images, and FIG. 3 is a flow chart of a mode of use of the process according to an embodiment of the invention.

DETAILED DESCRIPTION OF THE INVENTION

Although the invention is not limited thereto, an embodiment of the invention to the reconstruction of a three-dimensional angiographic image of a patient, particularly of his/her head, is now going to be described.

According to one embodiment, the digital two-dimensional projected images are acquired from detectors placed in different projection planes corresponding to the different positions of the camera. In practice, these different detections can be obtained by the rotation of a single detector around the object. Calibration of the camera, notably, provides calibration parameters (projection matrices) relative to the projection of voxels in these projection planes. For the rectification of each acquired two-dimensional image, the acquired two-dimensional image is projected in a rectified plane parallel to the specific axis chosen, a rectified frame of reference is defined in the rectified plane, one of the axes of which is parallel to the specific axis chosen, and rectification parameters (rectification matrices) are established, making it possible to determine the coordinates of each pixel of the acquired image in the associated rectified frame of reference, in order to establish the digital rectified image for the acquired image. The calibration parameters associated with each acquired image are then modified, taking into account the rectification parameters, for example, by making a simple matrix calculation between the initial projection matrices and the rectification matrices, so as to obtain modified or rectified projection matrices. The iterative algorithm of algebraic image reconstruction is applied between each rectified image and the set of voxels, taking into account the modified calibration parameters by successively treating the voxels situated on lines parallel to said specific axis chosen.

In other words, while in the prior art, the algebraic image reconstruction algorithm was applied directly between the set of voxels of the volume and the set of acquired two-dimensional images in the different original projection planes, the image reconstruction algorithm is applied according to the invention between images rectified in relation to those acquired images and the set of voxels of the volume by successively treating the voxels in a predetermined order, taking into account the choice of the specific axis of the calibration frame of reference.

More precisely, a rectified plane parallel to that specific axis and in which the acquired image is projected is defined from the original projection plane of an acquired image. The pixels of the rectified image are then found in a frame of reference of that rectified plane, one of the axes of which (abscissa axis or ordinate axis) is parallel to said specific axis, the rectification matrix making it possible to determine, in that rectified frame of reference, the coordinates of each pixel of the acquired image. The projection of voxels of the volume in the rectified frame of reference of each rectified image will then be carried out with the aid of the modified projection matrix.

In an embodiment of the invention two of the coefficients of the matrix are nil, which makes it possible, by successively treating the voxels in a predetermined order, to determine, knowing the projection of a current pixel, the projection of the following pixel with only one addition.

More precisely, if z designates the coordinate of a voxel according to the specific axis chosen, for example, the mean axis of rotation of the camera, and if x and y designate the other two coordinates of the voxel, the voxels with constant x and y will be treated by varying coordinate z in order.

Referring, in particular, to FIGS. 1 and 2, it can be seen that the imaging system usable for applying the invention makes it possible to obtain a set of two-dimensional acquired images IA1–IAn, in this case by rotation of an X-ray source 2 around an object 1, e.g., a patient's head. In fact, as is standard in angiography, each acquired image IA1 is a subtracted image which is, for example, obtained by a standard technique of logarithmic subtraction of two X-rays taken under the same incidence before and after an injection of a contrast product in the vascular tree, the three-dimensional image of which it is desired to reconstruct.

Each acquired image, e.g., IAi is obtained from a two-dimensional radiation detector, for example, of the luminance amplifier type used in radiology, arranged opposite the X-ray tube in a so-called projection plane PPi. The different projection planes are obtained by the different angular positions of the detector in rotation around the patient's head. The normal XOi in projection plane PPi defines the optical axis of the acquired image IAi. The detector is connected to treatment means 3 containing, notably, sampling means connected to a microprocessor incorporating software in its program memory associated with the algebraic image reconstruction algorithm used and, in general, all the functional means making possible use of the method according to the invention.

In the case of an X-ray imaging system composed of an X-ray source and a two-dimensional detector, the geometric operation taking place in production of the acquired image is a conic projection of a scanned object, deployed in a three-dimensional space, on a two-dimensional space which is that of the projection plane corresponding to the detection plane. The geometric parameters completely describing the different conic projections must be known. Now, it is often impossible and too imprecise to access these parameter directly, that is, for example, by directly measuring on the acquisition system the distance between the X-ray source and the detector.

The operation resulting in a precise indirect knowledge of the geometric parameters occurring in the production of an image is called imaging system calibration. The principle, standard and well known, is based on the use of a geometric shadow known in three-dimensional space and whose two-dimensional projection is acquired. More precisely, the calibration involves the following stages:

a known object is used, the calibration shadow presenting a number of characteristic points whose position in space is known by coordinates measured in relation to a marker proper to that object;

the image of that shadow is acquired under geometric conditions from a point of view (or incidence) that it is desired to calibrate;

the projections of the characteristic points in the image are recognized. For that purpose, each characteristic point of the object is associated with its trace in the projected acquired image;

the system of equation describing the projection is inverted in the mathematical sense;

and the set of parameters is finally obtained for the given point of view.

A form of geometric calibration shadow often used is that of a cube, with eight corners, on which metal balls opaque to X-rays are arranged. The calibration being an operation known to the expert, it will not be described more in detail, especially considering that several papers published have already described the principle of a manual geometric calibration. The following articles can, notably, be cited:

(1) D. L. Parker, J. Wu, D. L. Pope, R. Van Bree, G. R. Caputp and H. W. Marshall, "Three-dimensional reconstruction and flow measurements of coronary arteries using multiview digital angiography," *New Developments in Quantitative Coronary Arteriography*, J. C. Reiber and P. W. Serruys Eds., pp. 225–247, Kluwer Academic Publishers, 1988;

(2) D. J. Hawks, A. C. F. Colchester and C. R. Mol, "The accurate 3-D reconstruction of the geometric configuration of the vascular trees from X-ray recordings," *Physics and Engineering of Medical Imaging*, R. Guzzardi Ed., Nijhoff, 1987;

(3) M. Garreau, J. L. Coatrieux, R. Collorec and C. Chardenon, "A knowledge-based approach for 3-D reconstruction and labeling of vascular networks from biplane angiographic projections," *IEEE Medical Imaging*, Vol. 10, No. 2, pp.122–131, June 1991.

It is also possible to use a known method of automatic geometric calibration of an X-ray imaging system, such as that described in French Patent Application No. 93 00804. In short, for such automatic calibration, a shadow is used in which the balls are gradually distributed in a succession such that ball heights, measured along the axis of rotation of the imaging system, and especially a shadow axis, are monotones increasing (or decreasing) with a serial number of balls in the sequence.

Calibration of the imaging system makes it possible, notably, to determine the estimated mean axis Ax of rotation of the camera around the object, as well as the position of the source 2 and the geometric characteristics of the optical axes of the different acquired images. Calibration also makes it possible to define a virtual volume VV (intersection of the different projection cones) surrounding the object 1 and broken down into elementary volume elements Vi or "voxels." This volume VV, and therefore each voxel Vi, is spatially marked in a frame of reference, hereinafter called calibration frame of reference, one of the axes of which, axis Z in this case, is merged with the estimated axis of rotation Ax. It is to be noted here that the projection planes PPi in which the acquired images IAi are projected are not generally parallel to axis Z.

Calibration also makes it possible to define for each acquired image IAi a projection matrix Pi enabling the coordinates of its projection (pixel) in the corresponding acquired image IAi to be determined for each voxel Vi.

A mode of use of the method in an embodiment of the invention is described with reference, in particular, to FIG. 3. While according to the prior art the algebraic image reconstruction algorithm was applied directly on the acquired images IAi (obtained after calibration 30 and acquisition 31), in an embodiment of the invention performs a pretreatment or rectification 32 on the acquired images, so as to obtain rectified images IRi on which the three-dimensional image will be reconstructed.

More precisely, in order to obtain the rectified image IRi from the corresponding acquired image IAi, the optical axis XOi of the projection plane PPi of the acquired image IAi is projected in a plane perpendicular to axis Z and then the plane of the rectified image is defined as being the plane perpendicular to the projection of that optical axis XOi. The rectified plane in which the rectified image is going to be found is therefore parallel to axis Z. A rectified frame of reference is then defined in that rectified plane, one of the axes of which, e.g., the abscissa axis, is parallel to axis Z.

A rectification matrix making it possible to determine the coordinates of each pixel of the acquired image IAi in that rectified frame is reference is then defined. The new coordinates of those pixels thus define a digital rectified image IRi. The elementary geometric conversion calculations of the projections making it possible to pass from an acquired image to a rectified image and to elaborate the corresponding rectification matrix are standard calculations for the expert and have not been described more in detail above for the sake of simplification. This set of operations is carried out as software in the microprocessor of the treatment means.

With this rectification matrix, a modified projection matrix Qi is elaborated, obtained simply by a left-hand multiplication of the projection matrix Pi (obtained after calibration) by the rectification matrix.

The modified projection matrix Qi therefore makes it possible to determine the coordinates of the projection of each voxel Vi in the rectified frame of reference of the rectified image and to determine, consequently, whether that voxel is actually projected or not in that rectified image.

This modified projection matrix Qi is in the form:

$$\begin{pmatrix} l'_{11} & l'_{12} & l'_{13} & l'_{14} \\ l'_{21} & l'_{22} & 0 & l'_{24} \\ l'_{31} & l'_{32} & 0 & l'_{34} \end{pmatrix}$$

It is therefore observed that two of the coefficients of that matrix Qi, namely, coefficients $l_{23}$ and $l_{33}$, are nil.

The following stage of the procedure consists of reconstruction 33 of the three-dimensional image IF by applying the algebraic image reconstruction algorithm between the set of rectified images IRi and the set of voxels Vi of volume VV.

In that connection, a coefficient $\mu$ is assigned to each voxel Vi, which is initialized to an initial value, generally zero. Following the reconstruction stage, that is, after a predetermined number of iterations of the image reconstruction algorithm, a set of values will be obtained for all the coefficients $\mu$ associated with all the voxels of the volume. Each coefficient $\mu$ is representative of the position of the corresponding voxel in relation to a blood vessel. In fact, if the value $\mu$ assigned to a voxel is nil, then that voxel is not situated in a blood vessel, while an other than nil value of that coefficient signifies that the corresponding voxel is situated in a blood vessel. It will therefore be possible, by means of a standard visualization device, to reconstitute visually the three-dimensional image of the vascular tree situated in the patient's head from the set of values of the coefficients $\mu$ obtained.

In each iteration of the image reconstruction algorithm, each rectified image IRi is successively considered.

For each image IRi, one determines, first of all, the coordinates of the projection of each voxel Vi in the rectified frame of reference of image IRi by means of the modified projection matrix Qi. If the voxel Vi is actually projected in image IRi, that is, if the coordinates of the corresponding projected pixel are situated within the limits of the rectified image IRi, a gray level is then assigned to that projected pixel equal to the gray level of that pixel obtained on the previous iteration, plus the current value of the coefficient $\mu$ associated with voxel Vi. A virtual image IVi is thus defined, from which the rectified real image IRi is subtracted. A residual image is then obtained, each of the pixels of which is assigned to a residual gray level. A back projection or reverse projection is then made of that residual image in volume VV. In practice, for that back projection, the same projection calculations as those made in the previous projection stage are carried out on each voxel Vi of volume VV, but this time one modifies the value of coefficient $\mu$ associated with a voxel Vi which is actually projected in the residual image by adding to the present value $\mu$ of the voxel the residual value of the pixel corresponding to a near standardization coefficient.

Once these projection-back projection operations have been carried out for the set of voxels for a rectified image IRi, the same operations are performed for the following rectified image and all these operations are repeated a number of times, three in practice.

An embodiment of the invention, in combination with the pretreatment of acquired images having made it possible to obtain the rectified images, consists of successively treating the voxels Vi in a predetermined order.

More precisely, if x, y and z designate the coordinates of a voxel Vi, and if u and v designate the coordinates of projection of that voxel Vi in the rectified frame of reference of the corresponding rectified image, the coordinates u and v are obtained by the following formulas:

$$u = \frac{\lambda_1}{\lambda_3} \qquad v = \frac{\lambda_2}{\lambda_3}$$

where $\lambda_1$, $\lambda_2$ and $\lambda_3$ are defined by the following formulas:

$$\lambda_1 = {'}_{11}x + {'}_{12}y + {'}_{13}z + {'}_{14}$$

$$\lambda_2 = {'}_{22}x + {'}_{23}y + {'}_{24}$$

$$\lambda_2 = {'}_{32}x + {'}_{33}y + {'}_{34}$$

taking into account the fact that two of the coefficients of the modified projection matrix Qi are nil.

Also, if one seeks to determine the coordinates of projection of the following voxel, of coordinates (x, y, z+1), the coefficients $\lambda_1''$, $\lambda_2''$ and $\lambda_3''$ assigned to that following voxel are defined by the formulas:

$$\lambda_1'' = \lambda_1 + {'}_{13}$$

$$\lambda_2'' = \lambda_2$$

$$\lambda_3'' = \lambda_3$$

Consequently, the coordinates $u''$ and $v''$ of projection of that following voxel are defined by the formulas:

$$u'' = u + \frac{'13}{\lambda_3}$$

Therefore since $I_{13}$ and $\lambda_3$ are constant, determination of the coordinate un necessitates making only one addition of a constant to the coordinate u known and previously stored.

In other words, the voxels will be treated group by group, all of the voxels of a same group having their pair of coordinates (x, y) constant and, within a group, the third coordinate of the voxel will be successively varied. In other words, this means successively treating the voxels situated on lines parallel to axis z. On a same treatment line calculation of the projection of the current voxel, knowing the projection of the previous voxel, will necessitate only one addition. Of course, supplementary operations are, nevertheless, necessary on each change of treatment line, that is, when either of the other two coordinates x and y of a voxel is modified.

Various modifications in steps and/or functions and/or structure of the disclosed embodiments of the invention may be made by one skilled in the art without departing from the scope and extent of the claims.

What is claimed is:

1. Method of reconstruction of a three-dimensional image of an object from a set of digital two-dimensional projected images of the object obtained for different positions around the object, comprising the steps of:
   a. acquiring the set of digital two-dimensional projected images and a reconstruction of the three-dimensional image from the projected two-dimensional acquired images and an iterative algorithm of algebraic image reconstruction;
   b. calibrating the different position images for a volume containing the object and dividing into voxels, the space coordinates of which are identified in a chosen calibration frame of reference;
   c. applying a pretreatment on each acquired image in order to establish a rectified image having a predetermined spatial orientation selected as a function of a chosen specific axis of the calibration frame of reference; and
   d. applying the iterative algorithm of algebraic image reconstruction between each rectified image and the set of voxels by successively treating the voxels in a predetermined order linked to the choice of said specific axis, whereby a duration of reconstruction of the three-dimensional image is minimized.

2. Method according to claim 1, wherein the digital two-dimensional projected images are acquired from detectors placed in different projection planes corresponding to the different positions;

the calibration provides calibration parameters relative to the projection of voxels in the projection planes; in the pretreatment of each acquired two-dimensional image, the acquired two-dimensional image is projected in a rectified plane parallel to the specific axis chosen, a rectified frame of reference is defined in that rectified plane, one of the axes of which is parallel to the specific axis chosen, and rectification parameters are elaborated, making it possible to determine the coordinates of each pixel of the acquired image in the associated rectified frame of reference, in order to elaborate the digital rectified image for the acquired image, and the calibration parameters associated with each acquired image are modified, taking into account the rectification parameters, and applying the iterative algorithm of algebraic image reconstruction between each rectified image and the set of voxels, taking into account the modified calibration parameters by successively treating the voxels situated on lines parallel to said specific axis chosen.

3. Method according to claim 2, wherein an optical axis of each acquired image being determined on calibration, the rectified plane of an acquired image is determined as being the plane perpendicular to the projection of the optical axis of that acquired image in the plane perpendicular to the specific axis chosen.

4. Method according to claim 1 wherein the different projected images are obtained by a camera rotating around the object, calibration of the camera determines a mean estimated axis of rotation of the camera, and the mean estimated axis of rotation is chosen as specific axis of the calibration frame of reference.

5. Method according to claim 2 wherein the different projected images are obtained by a camera rotating around the object, calibration of the camera determines a mean estimated axis of rotation of the camera, and the mean estimated axis of rotation is chosen as specific axis of the calibration frame of reference.

6. Method according to claim 3 wherein the different projected images are obtained by a camera rotating around the object, calibration of the camera determines a mean estimated axis of rotation of the camera, and the mean estimated axis of rotation is chosen as specific axis of the calibration frame of reference.

7. Method according to claim 1 wherein the acquisition of each two-dimensional projected image entails a difference of two images of the object obtained before and after injection of a contrast product in the object, for a same position of the projected images.

8. Method according to claim 2 wherein the acquisition of each two-dimensional projected image entails a difference of two images of the object obtained before and after injection of a contrast product in the object, for a same position of the projected images.

9. Method according to claim 3 wherein the acquisition of each two-dimensional projected image entails a difference of two images of the object obtained before and after injection of a contrast product in the object, for a same position of the projected images.

10. Method according to claim 4 wherein the acquisition of each two-dimensional projected image entails a difference of two images of the object obtained before and after injection of a contrast product in the object, for a same position of the projected images.

11. Method according to claim 5 wherein the acquisition of each two-dimensional projected image entails a difference of two images of the object obtained before and after injection of a contrast product in the object, for a same position of the projected images.

12. Method according to claim 6 wherein the acquisition of each two-dimensional projected image entails a difference of two images of the object obtained before and after injection of a contrast product in the object, for a same position of the projected images.

* * * * *

UNITED STATES PATENT AND TRADEMARK OFFICE
CERTIFICATE OF CORRECTION

PATENT NO. : 6,320,928 B1
DATED : November 20, 2001
INVENTOR(S) : Régis Vaillant et al.

It is certified that error appears in the above-identified patent and that said Letters Patent is hereby corrected as shown below:

Column 6,
Lines 8-10, the matrix should appear as follows:

$$\begin{bmatrix} 1_{11} & 1_{12} & 1_{13} & 1_{14} \\ 1_{21} & 1_{22} & 0 & 1_{24} \\ 1_{31} & 1_{32} & 0 & 1_{34} \end{bmatrix}$$

Column 7,
Lines 11-13, the formulas should appear as follows:

$$\lambda_1 = 1_{11} X + 1_{12} Y + 1_{13} Z + 1_{14}$$
$$\lambda_2 = 1_{22} X + 1_{23} Y + \phantom{XXX} 1_{24}$$
$$\lambda_3 = 1_{32} X + 1_{33} Y + \phantom{XXX} 1_{34}$$

Line 24, the formula should appear as follows:
$$-- \lambda_1^n = \lambda_1 + 1_{13} --$$
Line 25, the formula should appear as follows:
$$-- \lambda_3^n = \lambda_3 --$$
Lines 31-32, the formula should appear as follows:
$$u^n = u + \frac{1_{13}}{\lambda_3}$$

Signed and Sealed this

Twenty-eighth Day of June, 2005

JON W. DUDAS
*Director of the United States Patent and Trademark Office*